United States Patent
Weferling et al.

(10) Patent No.: US 6,359,171 B1
(45) Date of Patent: Mar. 19, 2002

(54) PROCESS FOR PREPARING DIALKYLPHOSPHINIC ACIDS AND THEIR SALTS

(75) Inventors: Norbert Weferling, Hürth; Martin Sicken, Köln; Günter Kolbe, Kerpen-Türnich; Hans-Peter Schmitz, Brühl, all of (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/577,463

(22) Filed: May 24, 2000

(30) Foreign Application Priority Data

May 25, 1999 (DE) ......................................... 199 23 619

(51) Int. Cl.$^7$ .................................................. C07F 9/30
(52) U.S. Cl. .............................. 562/8; 558/89; 558/104
(58) Field of Search ................................. 562/8; 558/89, 558/104

(56) References Cited

U.S. PATENT DOCUMENTS

| | | | |
|---|---|---|---|
| 3,534,127 A | | 10/1970 | Spivack |
| 3,563,948 A | | 2/1971 | Spivack |
| 3,742,096 A | | 6/1973 | Spivack |
| 3,914,345 A | * | 10/1975 | Kleiner et al. |
| 4,036,811 A | | 7/1977 | Noetzel et al. |
| 4,521,348 A | | 6/1985 | Finke et al. |
| 4,740,332 A | * | 4/1988 | Thottathil |
| 4,939,285 A | | 7/1990 | Weis et al. |
| 4,972,011 A | | 11/1990 | Richardson et al. |
| 4,973,727 A | | 11/1990 | Gainer et al. |
| 5,780,534 A | * | 7/1998 | Kleiner et al. ............... 524/133 |
| 5,830,973 A | | 11/1998 | Horold et al. |
| 5,869,722 A | * | 2/1999 | Kleiner ........................ 556/174 |
| 5,973,194 A | * | 10/1999 | Weferling et al. ............. 562/8 |
| 6,011,172 A | * | 1/2000 | Weferling et al. ............. 562/8 |
| 6,013,707 A | * | 1/2000 | Kleiner et al. ............... 524/126 |
| 6,090,967 A | * | 6/2000 | Horold et al. ................ 558/105 |
| 6,090,968 A | * | 7/2000 | Horold et al. ................ 558/137 |
| 6,096,914 A | * | 8/2000 | Seitz ........................... 556/14 |

FOREIGN PATENT DOCUMENTS

| | | |
|---|---|---|
| DE | 24 47 727 | 4/1976 |
| DE | 198 51 768 | 6/1999 |
| DE | 197 52 736 | 8/1999 |
| DE | 198 28 861 | 12/1999 |
| EP | 0 011 245 | 5/1980 |
| EP | 0 245 207 | 11/1987 |
| EP | 0 299 922 | 1/1989 |
| EP | 0 327 496 A3 | 8/1989 |
| EP | 0 327 496 A2 | 8/1989 |
| EP | 0 327 496 B1 | 8/1989 |
| EP | 0 699 708 B1 | 3/1996 |
| EP | 0 699 708 A3 | 3/1996 |
| EP | 0 699 708 A2 | 3/1996 |
| EP | 0 969 008 | 1/2000 |
| FR | 1 558 606 | 1/1968 |
| WO | WO 98/20012 | 5/1998 |
| WO | WO 99/28327 | 6/1999 |
| WO | WO 99/28328 | 6/1999 |
| WO | WO 99/28329 | 6/1999 |

OTHER PUBLICATIONS

CA:69:67487 abs of Khim Org Soedin Fosfora Akad Nauk SSSR Otd Obsch Tekh Kim by Petrov et al 181–6, 1967.*
CA:131:5381 abs of WO992837, Jun. 1999.*
Derwent Patent Family Abstract for WO 98/20012 (May 14, 1998).
Derwent Patent Family Abstract for WO 99/28327 (Jun. 10, 1999).
Derwent Patent Family Abstract for WO 99/28328 (Jun. 10, 1999).
William C Drinkard: "Some salts of symmetrick phosphinic acids", Journal of the American Chemical Society, Nov. 1, 1952, p5520–5521.
Radikalische Initiierung mit Chemischen Initiatoren [Polymerization by free–radical initiation], Houben–Weyl, Supplementary vol. 20, pp. 15–74 (1986).
Houben–Weyl IV (1981), vol. XII/1 (1963), pp. 220–240.
Houben–Weyl, vol. 12/1, p. 306 (1963).
English Translation of abstract of EP 0 699 708; Jun. 3, 1996.
Petrov, V.V., Dialkylphosphinic Acids, Khim. Org. Soedin. Fosfora, Akad. Nauk SSSR, Otd. Obshch. Tekh. Khim. 1967 181–6, Document No. 69:67487.

* cited by examiner

Primary Examiner—Jean F. Vollano
(74) Attorney, Agent, or Firm—Anthony A. Bisulca

(57) ABSTRACT

The invention relates to a process for the preparation of dialkylphosphinic acids and salts thereof, which comprises a) reacting elemental yellow phosphorus with alkylating agents in the presence of a base to give a mixture which comprises, as principal constituents, the (metal) salts of alkylphosphonous, phosphorous and hypophosphorous acids, b) esterifying the principal constituents of the mixture from a) to give an ester mixture, c) isolating the ester of the alkylphosphonous acid from the ester mixture, d) preparing the corresponding ester of the dialkylphosphinic acid from the ester of the alkylphosphonous acid by free-radical-initiated reaction with olefins, e) converting the ester of the dialkylphosphinic acid into the free acid or into the dialkylphosphinic acid salts of metals from groups IA, IIA, IIIA, IVA, VA, IIB, IVB, VIIB or VIIIB of the Periodic Table or of cerium.

The invention likewise relates to the use of the dialkylphosphinic acids/salts prepared by this process for the preparation of various products, in particular flame retardants.

41 Claims, No Drawings

PROCESS FOR PREPARING DIALKYLPHOSPHINIC ACIDS AND THEIR SALTS

BACKGROUND OF THE INVENTION

The invention relates to a process for the preparation of dialkylphosphinic acids and salts thereof, and to the use of the dialkylphosphinic acids and salts thereof prepared by this process.

Phosphinic acids and salts thereof can be prepared by various methods and have been described in large number (Houben-Weyl IV, Vol. XII/1, pp. 220 to 240).

The preparation of these compounds is technically complex and is carried out, for example, by oxidation of the corresponding phosphines or via the esters of alkylphosphonous acids, which are themselves prepared from the corresponding phosphonous acid dihalides by reaction with alcohols. The phosphines and phosphonous acid dihalides, for example methyldichlorophosphine, on which the process is based have hitherto been prepared by complex syntheses (Houben-Weyl, Volume 12/1, p. 306). In addition, various by-products are formed which, like some of the abovementioned starting materials too, are toxic, self-igniting and/or corrosive, i.e. are highly undesired.

The organic phosphinic acids and salts thereof based on the abovementioned starting materials, and processes for their preparation and use have in some cases been described.

Thus, for example, the aluminum salts of organic phosphoric acids are known as flame retardants. They can be prepared by various processes.

EP-A-0 299 922 describes a process for the preparation of aluminum salts of phosphoric and phosphonic acid esters by reacting aluminum compounds with phosphoric acid, phosphonic acid or an ester thereof.

In the process described in EP-A-0 245 207, aluminum compounds are reacted with alkylphosphonic acid diesters to give the corresponding aluminum salt.

According to EP-A-0 327 496, the reaction of aluminum hydroxide with alkylphosphonic acid diesters at about 180° C. in the absence of water likewise results in aluminum salts of the phosphonic acid monoesters.

EP-A-0 699 708 describes flame-retardant polyester molding compositions in which the polyesters have been rendered flame-resistant by the addition of calcium salts or aluminum salts of phosphinic or diphosphinic acids. The abovementioned salts are obtained by reacting the corresponding dialkylphosphinic acids with calcium hydroxide or aluminum hydroxide.

DE-A-24 47 727 describes flame-retardant polyamide molding compositions which comprise a (metal) salt of a phosphinic acid or of a diphosphinic acid.

SUMMARY OF THE INVENTION

However, the abovementioned processes have the disadvantage that the suitable organophosphorus compounds first of all have to be prepared in an inconvenient manner. This is particularly true of the dialkylphosphinic acids, whose aluminum salts are highly suitable for use as flame retardants in certain polymers.

The object of the invention was therefore to provide a process for the preparation of dialkylphosphinic acids and salts thereof in which both the dialkylphosphinic acids themselves and the likewise desired end products, namely dialkylphosphinic acid salts of certain metals, can be prepared in a particularly simple and economical manner.

There is therefore a need for a process for the preparation of dialkylphosphinic acids and salts thereof which can be carried out in a simple manner and in which uniform products are obtained in high yield. A process of this type should also be significantly superior to the processes known hitherto in economic and environmental terms.

DESCRIPTION OF THE PREFERRED EMBODIMENTS

This object is achieved by a process of the type mentioned at the outset which comprises
a) reacting elemental yellow phosphorus with alkylating-agents in the presence of a base to give a mixture which comprises, as principal constituents, the (metal) salts of alkyl-phosphonous, phosphorous and hypophosphorous acids,
b) esterifying the principal constituents of the mixture from a) to give an ester mixture,
c) isolating the ester of the alkylphosphonous acid from the ester mixture,
d) preparing the corresponding ester of the dialkylphosphinic acid from the ester of the alkylphosphonous acid by free-radical-initiated reaction with olefins,
e) converting the ester of the dialkylphosphinic acid into the free acid or into the dialkylphosphinic acid salts of metals from groups IA, IIA, IIIA, IVA, VA, IIB, IVB, VIIB or VIIIB of the Periodic Table or of cerium.

The process according to the invention has the considerable advantages over the processes known hitherto that it has a positive balance in the product distribution and at the same time avoids the phosphine and phosphonous acid dihalide starting materials, which are regarded as undesired, and in addition produces no halogenated organic by-products.

The alkylating agents are preferably alkyl halides, dialkyl sulfates, trialkyl phosphates, dialkyl carbonates and/or formic acid ortho-esters.

The alkylating agents are particularly preferably methyl chloride, methyl bromide and/or dimethyl sulfate.

The bases are preferably hydroxides, carbonates, bicarbonates, amides, alkoxides and/or amine bases, such as, for example, amines and ammonia.

The reaction in step a) is preferably carried out in a two-phase system comprising aqueous alkali or alkaline-earth metal hydroxide or mixtures thereof and an organic solvent.

The organic solvents employed in step a) are preferably straight-chain or branched alkanes, alkyl-substituted aromatic solvents, water-immiscible or only partially water-miscible alcohols or ethers, alone or in combination with one another.

The organic solvent employed is particularly preferably toluene, alone or in combination with alcohols.

The reaction can, if desired, also be carried out in a non-aqueous system, for example by using solid sodium hydroxide or amines.

The reaction is preferably carried out in the presence of a phase-transfer catalyst.

The phase-transfer catalyst is preferably a tetraalkylphosphonium halide, triphenylalkylphosphonium halide or tetraorganylammonium halide.

The temperature during the reaction is preferably from −20 to +80° C.

The temperature is particularly preferably from −10 to +30° C.

The reaction is preferably carried out under a pressure of from 0 to 10 bar.

Step a) of the process according to the invention is preferably carried out by suspending or dissolving the yellow phosphorus in a solvent or solvent mixture and then reacting it with an alkyl halide and a compound of the formula MOH or M'(OH)$_2$ or mixtures thereof, where M is an alkali metal and M' is an alkaline-earth metal.

The yellow phosphorus and the alkyl halide are preferably reacted with one another in a molar ratio of from 1:1 to 1:3, where the molar ratio of yellow phosphorus to the compound of the formula MOH or M'(OH)$_2$ is from 1:1 to 1:5.

The principal constituents of the mixture from a) are preferably esterified in step b) using a linear or branched alcohol of the general formula R—OH, where R is a linear or branched alkyl radical having 1 to 10 carbon atoms.

In another preferred embodiment of the process according to the invention, the principal constituents of the mixture from a) are converted into a mixture of alkylphosphonous, phosphorous and hypophosphorous acids using mineral acids, with the (metal) salts of the mineral acids simultaneously being precipitated, and the mixture of these acids subsequently being esterified.

The water formed during the esterification is preferably removed by azeotropic distillation.

In other words, the esterification of the phosphonous acid to the corresponding monoester can be achieved by reaction with relatively high-boiling alcohols with removal of the resultant water by azeotropic distillation.

The precipitation of the metal salts, usually the alkali or alkaline-earth metal mineral salts, is preferably carried out here by replacement of the solvent water by the alcohol to be used in reaction step b).

The alkali or alkaline-earth metal mineral salt which has already precipitated is preferably filtered off before the esterification.

The alcohol is preferably n- or i-butanol, n-hexanol, ethylhexanol and/or amyl alcohol.

The mineral acid is preferably hydrochloric acid, sulfuric acid and/or phosphoric acid.

The mineral acid is particularly preferably hydrochloric acid.

The phosphines formed in small amounts during step a) are preferably removed by oxidation.

Hydrogen peroxide is preferably used as oxidant.

The ester of the alkylphosphonous acid is preferably removed by distillation in step c). The ester of the alkylphosphonous acid is preferably n-butyl methylphosphonite, isobutyl methylphosphonite, n-hexyl methylphosphonite, 2-ethylhexyl methylphosphonite and/or amyl methylphosphonite.

The free-radical initiators employed are preferably azo compounds or- peroxidic inorganic and/or peroxidic organic free-radical initiators.

The azo compounds are preferably cationic and/or non-cationic azo compounds.

The cationic azo compounds employed are preferably 2,2'-azobis(2-amidinopropane) dihydrochloride or 2,2-azobis(N,N'-dimethyleneisobutyramidine) dihydrochloride.

The non-cationic azo compounds employed are preferably azobis(isobutyronitrile), 4,4'-azobis(4-cyanopentanoic acid) or 2,2'-azobis(2-methylbutyronitrile).

The peroxidic inorganic free-radical initiators employed are preferably hydrogen peroxide, ammonium peroxodisulfate and/or potassium peroxodisulfate.

The peroxidic organic free-radical initiators employed are preferably dibenzoyl peroxide, di-tert-butyl peroxide and/or peracetic acid.

A broad selection of suitable free-radical initiators is given, for example, in Houben-Weyl, Supplementary Volume 20, in the chapter "Polymerization by free-radical initiation" on pages 15–74.

The free-radical initiators are preferably metered in continuously during the reaction.

The free-radical initiators are preferably metered in continuously during the reaction as a solution in the olefin employed.

The olefins employed in step d) are preferably linear or branched α-olefins. The olefins employed are preferably those having an internal double bond, cyclic or open-chain dienes and/or polyenes having 2 to 20 carbon atoms.

The olefins employed are preferably ethylene, n- or i-propylene, n- or i-butene, n- or i-pentene, n- or i-hexene, n- or i-octene, 1-decene, 1,5-cyclooctadiene, 1,3-cyclopentadiene, dicyclopentadiene and/or 2,4,4-trimethylpentene isomer mixtures.

The olefins preferably carry a functional group.

Suitable olefins are compounds of the general formula $$\begin{array}{c}R^1\\R^2\end{array}\!\!\!C\!=\!C\!\!\!\begin{array}{c}R^3\\R^4\end{array}$$

in which $R^1$–$R^4$ may be identical or different and are hydrogen, an alkyl group having 1 to 18 carbon atoms, phenyl, benzyl or an alkyl-substituted aromatic radical.

Likewise suitable are cycloolefins of the formula $$\underset{(CH_2)_n}{\overset{\frown}{\bigg(}\!\!\!=\!\!\!\bigg)}$$

in particular cyclopentene, cyclohexene, cyclooctene and cyclodecene.

It is also possible to employ open-chain dienes of the formula $$\begin{array}{c}R^5\\R^6\end{array}\!\!\!C\!=\!\overset{R^7}{\underset{}{C}}\!-\!R^{11}\!-\!\overset{R^8}{\underset{}{C}}\!=\!C\!\!\!\begin{array}{c}R^9\\R^{10}\end{array}$$

in which $R^5$–$R^{10}$ are identical or different and are hydrogen or a $C_1$- to $C_6$-alkyl group, and $R^{11}$ is $(CH_2)_n$, where n=0 to 6. Preference is given here to butadiene, isoprene and 1,5-hexadiene.

Preferred cyclodienes are 1,3-cyclopentadiene, dicyclopentadiene and 1,5-cyclooctadiene, as well as norbornadiene.

The reaction with the olefins is preferably carried out at a temperature of from 40 to 250° C.

This reaction is particularly preferably carried out at a temperature of from 70 to 190° C.

This reaction is preferably carried out without a solvent.

Alternatively, it is also possible to carry out the reaction in the presence of a solvent.

The reaction is preferably carried out in an acetic-acid medium.

The reaction is preferably carried out under pressure.

The metals are preferably Li, Na, K, Mg, Ca, Sr, Ba, Al, Ge, Sn, Sb, Bi, Zn, Ti, Zr, Mn, Fe and/or Ce.

In step e), the ester of the dialkylphosphinic acid is preferably reacted directly with metal compounds to give metal salts of the dialkylphosphinic acid.

In step e), the ester of the dialkylphosphinic acid is preferably hydrolyzed to the dialkylphosphinic acid.

In step e), the ester of the dialkylphosphinic acid is preferably hydrolyzed to the dialkylphosphinic acid and subsequently converted into metal salts of the dialkylphosphinic acid.

In step e), the ester of the dialkylphosphinic acid is preferably hydrolyzed to the sodium salt of the dialkylphosphinic acid using sodium hydroxide solution.

In step e), the ester of the dialkylphosphinic acid is preferably hydrolyzed to the sodium salt of the dialkylphosphinic acid using sodium hydroxide solution and subsequently converted into metal salts of the dialkylphosphinic acid.

The reaction in step e) is preferably carried out after an optimum pH range for the salt precipitation has been established for the respective dialkylphosphinic acid/metal compound system.

The metal compounds are preferably metal oxides, hydroxides, oxide hydroxides, sulfates, acetates, chlorides, nitrates and/or alkoxides.

The metal compounds are particularly preferably aluminum hydroxide or aluminum sulfates.

The present invention also relates, in particular, to a process in which yellow phosphorus is reacted with methyl chloride in the presence of sodium hydroxide solution and the phase-transfer catalyst tributylhexadecylphosphonium bromide to give the sodium salt of methylphosphonous acid, the free acid is liberated therefrom by addition of hydrochloric acid, the free acid is esterified in the mixture using 2-ethylhexanol, the ester is isolated by distillation and subsequently reacted with ethylene with free-radical initiation by di-tert-butyl peroxide to give the corresponding ester of methylethylphosphinic acid and finally successively hydrolyzed with sodium hydroxide solution and precipitated as the aluminum salt of methylethylphosphinic acid using aluminum sulfate.

The invention also relates to the use of the dialkylphosphinic acids/salts prepared by the process according to the invention as precursors for chemical synthesis.

The invention also relates to the use of the dialkylphosphinic acids/salts prepared by the process according to the invention for the preparation of other phosphorus-containing compounds and derivatives, in particular as starting materials for crop protection agents.

The invention also relates to the use of the dialkylphosphinic acids/salts prepared by the process according to the invention as flame retardants and as starting materials for the preparation of flame retardants.

The invention relates to the use of the dialkylphosphinic acids/salts prepared by the process according to the invention as starting materials for the preparation of flame retardants for thermoplastic polymers, such as polyethylene terephthalate, polybutylene terephthalate or polyamide.

The invention also relates to the use of the dialkylphosphinic acids/salts prepared by the process according to the invention as starting materials for the preparation of flame retardants for thermosetting resins, such as unsaturated polyester resins, epoxy resins, polyurethanes or acrylates.

Surprisingly, it has been found that elemental yellow phosphorus can, after step a) of the process according to the invention, be reacted with alkylating agents in a two-phase system (organic solvent/base) and, if desired, in the presence of a (phase-transfer) catalyst under extremely mild conditions to give the (metal) salt of the corresponding alkylphosphonous acid RP(:O)HOH.

In addition, small amounts of dialkylphosphinic acids, trialkylphosphine oxide R$_3$P(:O), dialkylphosphine oxide and unidentified phosphorus compounds may be formed; these can be removed from the product mixture in the usual manner. A further by-product formed is hydrogen, which can easily be separated off from the reaction mixture. The abovementioned dialkylphosphinic acids can be separated off from the reaction mixture and employed or further processed elsewhere.

Surprisingly, neither phosphine (PH$_3$) nor alkylphosphines (RPH$_2$, R$_2$PH) are formed in significant amounts in the process according to the invention. Through the choice of suitable reaction conditions—such as the addition of small amounts of alcohols to the organic phase—the formation of all unidentified phosphorus-containing by-products is minimized to a surprisingly low content of a few mol % of the yellow phosphorus employed, in favor of the main product, the (metal) salts of alkylphosphonous acid.

The process according to the invention can be carried out, for example, by initially introducing the solvent together with the phase-transfer catalyst and, if necessary, warming the mixture to above the melting point of the yellow phosphorus, then adding the elemental (yellow) phosphorus, cooling the mixture to temperatures of, for example, from −10 to +30° C. with vigorous stirring, and subsequently adding the alkylating agent.

The reaction is initiated by addition of the base. When the reaction is complete, the reaction system can be diluted, for example with water, and the readily volatile components (H$_2$, PH$_3$, RPH$_2$, R$_2$PH and excess alkylating agent, etc.) are subsequently removed.

This gives a base-containing/organic two-phase system, whose phases are separated. The contents from the phases are determined analytically.

The reactants can also be combined in a different sequence, for example by introducing them continuously into a reactor (pressure tube, pressure reactor or cascade) in the above-defined molar ratio and removing them from the reactor again after a residence time of from 0.5 to 2 hours. The organic phase obtained after phase separation, which still contains the majority of any phase-transfer catalyst employed, is advantageously recycled.

The isolation of the pure alkylphosphonous acids from the mixture is carried out in a particularly simple manner via the corresponding esters, which, in contrast to the salts and acids of the alkylphosphonous acids, can be isolated from the mixture in a gentle manner by distillation. Although all other compounds present in the mixture are also partially esterified in steps b) and c) of the process according to the invention, they do not, however, form readily distillable products, and consequently the removal of the alkylphosphonous acid esters is achieved in surprisingly complete and pure form.

EXAMPLES

The invention is explained by the examples below:

Example 1

Aluminum Salt of Methylethylphosphinic Acid a1) Reaction of Yellow Phosphorus with Methyl Chloride

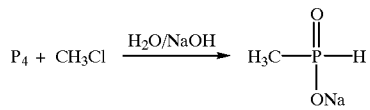

A solution of 26.1 g (0.05 mol) of tributylhexadecylphosphonium bromide in 1000 ml of toluene was introduced into a 5 l stainless-steel pressure reactor and pre-heated to 60° C. After 62 g (2 mol) of yellow phosphorus had been added, the mixture was cooled to −10° C. with vigorous stirring, and 202 g (4 mol) of methyl chloride were then condensed in. 400 g of 50% aqueous sodium hydroxide solution were then metered in over the course of 2 hours, during which the temperature was held at −10° C. 400 g of water were added over the course of a further hour, the mixture was then stirred for a further hour and warmed to room temperature, and the reactor was subsequently decompressed via combustion. Two homogeneous liquid phases were obtained, which were separated and analyzed.

The aqueous phase (weight: 920 g) contained 65.6 mol % of methylphosphonous acid, 14.9 mol % of phosphorous acid, 13.7 mol % of hypophosphorous acid and 2.8 mol % of dimethylphosphinic acid in the form of their sodium salts and 3 mol % of dimethyldiphosphine.

a2) Conversion of the Sodium Salts into the Acids/NaCl Removal

In succession, 60 g of 5% aqueous hydrogen peroxide solution, 240 g of 36% hydrochloric acid and 400 g of 2-ethylhexanol were added to the solution. After the water formed had been removed by distillation on a water separator, the precipitated sodium chloride was filtered off and washed with 100 g of 2-ethylhexanol. The ethylhexanol solutions now contained the compounds mentioned under a1) as the free acids.

b) Esterification of Methanephosphonous Acid in the Reaction Mixture Using 2-ethylhexanol:

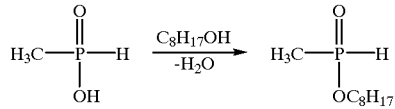

The ethylhexanol solutions from step a2) were combined and heated at about 120° C. for 6 hours on a water separator under slightly reduced pressure.

c) Isolation of the 2-ethylhexyl Methanephosphonite

The esterified reaction mixture from b) was subsequently freed from excess ethylhexanol by distillation and subjected to a vacuum distillation. At a pressure of 0.3 mm and a head temperature of 75° C., 220 g of 2-ethylhexyl methanephosphonite passed over. The product was obtained in the form of a clear, colorless liquid in a purity of greater than 99%, corresponding to a yield of 58%, based on the yellow phosphorus employed. Analyses: 16.0% of phosphorus (theory: 16.2%); $^{31}$P-NMR: doublet at 34 ppm (diastereomer pair)

d) Reaction with Ethylene to Give the Methylethylphosphinic Acid Ester

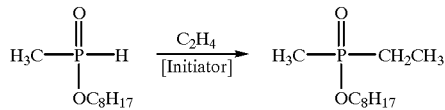

190 g of 2-ethylhexyl methanephosphonite from c) were introduced into a PTFE-coated 750 ml steel autoclave. The mixture was subsequently heated to 150° C., and ethylene at 5 bar was injected. With the ethylene pressure held constant, a solution of 3 g of di-tert-butyl ether in 30 g of 2-ethylhexyl methanephosphonite from c) was metered in at 150° C. over a period of 4 hours. After a post-reaction time of 1 hour, the autoclave was decompressed and the reactor contents analyzed by $^{31}$P-NMR spectroscopy:

61 ppm: methylethylphosphinic acid ester 97.3 mol %

62 ppm: methylbutylphosphinic acid ester 2.0 mol %

34 ppm: methylphosphonous acid ester: 0.7 mol %

258 g (yield>99%) of the phosphinic acid ester were obtained in the form of a clear, colorless liquid.

e) Hydrolysis of the Methylethylphosphinic Acid Ester to the Sodium Salt and Precipitation as the Al Salt

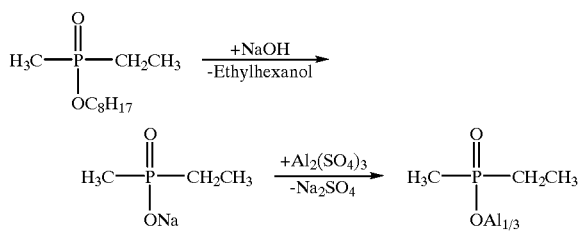

258 g of ethylhexyl methylethylphosphinite (1.2 mol) from d) were heated at 140° C. for 2 hours in a PTFE-coated 750 ml steel autoclave together with a solution of 47 g of NaOH (1.2 mol) in 200 g of water. After the resultant alcohol had been removed by distillation via a water separator, a further 400 ml of water were added, and a solution of 133 g (0.2 mol) of Al$_2$(SO$_4$)$_3$ · 18H$_2$O in 150 ml of water was subsequently metered in over a period of 60 minutes. After the resultant precipitate had been filtered off and dried at 30 mbar/130° C., 135 g of the aluminum salt of methylethylphosphinic acid were obtained in the form of a fine white powder. The phosphorus analysis gave 26.5% of P (calc.: 26.7%), and the aluminum analysis gave 8.1% of Al (calc.: 8.0%).

The yield in step f) is 97%, and the overall yield (steps a) to f)), based on the yellow phosphorus employed, is 56%.

Example 2

Aluminum Salt of Methylbutylphosphinic Acid 220 g of 2-ethylhexyl methanephosphonite were prepared analogously to Example 1, sub-steps a1) to c), and reacted with n-butene under the conditions as described in Example 1, sub-step d), to give 290 g of 2-ethylhexyl methylbutylphosphinate. This was subsequently heated at 220° C. for 10 hours together with 31 g of aluminum hydroxide and 300 ml of acetic acid. After cooling to room temperature, filtration and drying at 130° C. in a water-pump vacuum, 155 g of aluminum methylbutylphosphinate, corresponding to 92% of theory, based on the final reaction, or 53%, based on yellow phosphorus, were obtained. The phosphorus analysis gave 21.5% of P (calc.: 21.5%), the aluminum analysis gave 6.4% of Al (calc.: 6.2%).

Example 3

Zinc Salt of Methylethylphosphinic Acid a1)–d): i-Butyl Methylethylphosphinite:

A solution of 26.1 g (0.05 mol) of tributylhexadecylphosphonium bromide in 1000 ml of toluene was introduced into a 5 l stainless-steel pressure reactor and pre-heated to 60° C.

After 62 g (2 mol) of yellow phosphorus had been added, the mixture was cooled to 5° C. with vigorous stirring, and 202 g (4 mol) of methyl chloride were then condensed in. The mixture was then warmed to about 20° C., and 500 g of 40% aqueous sodium hydroxide solution were then metered in at this temperature over the course of 2 hours. 300 g of water were added over the course of one hour, the mixture was then stirred for a further two hours, and the reactor was subsequently decompressed via combustion. Two homogeneous liquid phases were obtained, which were separated. In succession, 60 g of 5% aqueous hydrogen peroxide solution, 240 g of 36% hydrochloric acid and 300 g of isobutanol were added to the aqueous phase (weight: 920 g containing 64.6 mol % of sodium methylphosphonite). After the water formed had been removed by distillation on a water separator, the precipitated sodium chloride was filtered off and washed with 100 g of i-butanol. The butanol solutions were combined and heated at 115–125° C. for 12 hours on a water separator. The esterified reaction mixture was subsequently freed from excess butanol by distillation and subjected to vacuum distillation. At a pressure of 0.5 mm and a head temperature of 42° C., 158 g of i-butyl methanephosphonite passed over in the fqrm of a clear, colorless liquid in a purity of greater than 99%. 128 g of the ester were subsequently heated to 150° C. in a PTFE-coated 750 ml steel autoclave, and ethylene at 5 bar was injected. With the ethylene pressure held constant, a solution of 3 g of di-tert-butyl ether in the remaining 30 g of i-butyl methanephosphonite was metered in at 150° C. over a period of 4 hours. After a post-reaction time of 1 hour, the autoclave was decompressed, giving 190 g (yield>99%) of the phosphinic acid ester in the form of a clear, colorless liquid.

e) Zinc Salt Preparation:

32 g (0.2 mol) of i-butyl methylethylphosphinate obtained were heated at 140° C. for 2 hours in a 300 ml steel autoclave together with a solution of 7.8 g of NaOH (0.2 mol) in 50 g of water. After the alcohol formed had been removed by distillation via a water separator, a further 80 ml of water were added, and a solution of 25 g (0.1 mol) of $ZnSO_4 \cdot 7H_2O$ in 40 ml of water was subsequently metered in over a period of 60 minutes. After the resultant precipitate had been filtered off and dried at 30 mbar/130° C., 23 g of the zinc salt of methylethylphosphinic acid were obtained in the form of a fine white powder. The phosphorus analysis gave 25.0% of P (calc.: 25.4%), the zinc analysis 12.5% of Zn (calc.: 12.3%).

Example 4

Lithium Salt of Methylethylphosphinic Acid 32 g (0.2 mol) of i-butyl methylethylphosphinate obtained as described in Example 3, sub-steps a1)–d), were heated at 140° C. for 2 hours in a 300 ml steel autoclave together with a solution of 8.4 g of LiOH. $H_2O$ (0.2 mol) in 50 g of water. After the resultant isobutanol and the water had been removed by distillation and the residue had subsequently been dried at 30 mbar/130° C., 23 g (>99% yield) of the lithium salt of methylethyl-phosphinic acid were obtained in the form of a white solid. The phosphorus analysis gave 27.0% of P (calc.: 27.2%), the lithium analysis 6.0% of Li (calc.: 6.1%).

Example 5

Sodium Salt of Methylethylphosphinic Acid 32 g (0.2 mol) of i-butyl methylethylphosphinate obtained as described in Example 3, sub-steps a1)–d), were heated at 140° C. for 2 hours in a 300 ml steel autoclave together with a solution of 8.0 g of NaOH. $H_2O$ (0.2 mol) in 20 g of water. After the resultant isobutanol and the water had been removed by distillation and the residue had subsequently been dried at 30 mbar/130° C., 26 g (>99% yield) of the sodium salt of methylethylphosphinic acid were obtained in the form of a white solid. The phosphorus analysis gave 23.5% of P (calc.: 23.8%), the sodium analysis 18.0% of Na (calc.: 17.7%).

Example 6

Methylethylphosphinic Acid 94 g (0.6 mol) of i-butyl methylethylphosphinate obtained as described in Example 3, sub-steps a1)–d), were heated at 140° C. for 8 hours in a 300 ml steel autoclave with 150 g of water. After the resultant isobutanol and the water had been removed by distillation followed by vacuum distillation, 58 g of methylethylphosphinic acid were obtained in the form of a clear, colorless liquid (90% yield; b.p.: 110° C./0.5 bar). The phosphorus analysis gave 28.1% of P (calc.: 28.7%).

Example 7

Magnesium Salt of Methylethylphosphinic Acid 27 g (0.25 mol) of methylethylphosphinic acid obtained as described in Example 6 were metered at room temperature over the course of 30 minutes into a suspension of 7.3 g (0.125 mol) of magnesium hydroxide in 100 g of water. A clear solution formed which, after removal of the water by distillation followed by drying at 30 mbar/130° C., gave 29.5 g (>99% yield) of the magnesium salt of methylethylphosphinic acid in the form of a white solid. The phosphorus analysis gave 25.9% of P (calc.: 26.0%), the magnesium analysis 10.0% of Mg (calc.: 10.2%).

Example 8

Iron(III) Salt of Methylethylphosphinic Acid 27 g (0.25 mol) of methylethylphosphinic acid obtained as described in Example 6 were metered at room temperature over the course of 30 minutes into a solution of 16.7 g (0.042 mol) of $Fe_2(SO_4)_3$ in 100 g of water. After the resultant precipitate had been filtered off and the residue had been dried at 30 mbar/130° C., –13.5 g of the iron(III) salt of methylethylphosphinic acid were obtained in the form of a fine white powder (85% yield). The phosphorus analysis gave 25.0% of P (calc.: 24.7%), the iron analysis 14.5% of Fe (calc.: 14.8%).

What is claimed is:

1. A process for the preparation of dialkylphosphinic acids and salts thereof, which comprises
   a) reacting elemental yellow phosphorus with alkylating agents in the presence of a base to give a mixture which comprises, as principal constituents, metal salts of alkylphosphonous, phosphorous and hypophosphorous acids,
   b) esterifying the principal constituents of the mixture from a) to give an ester mixture,
   c) isolating the ester of the alkylphosphonous acid from the ester mixture,
   d) preparing a corresponding ester of the dialkylphosphinic acid from the ester of the alkylphosphonous acid by free-radical-initiated reaction with olefins, and e) converting the ester of the dialkylphosphinic acid into a free acid or into dialkylphosphinic acid salts of cerium or metals from groups IA, IIA, IIIA, IVA, VA, IIB, VIIB or VIIIB of the Periodic Table.

2. The process as claimed in claim 1, wherein the alkylating agents are alkyl halides, dialkyl sulfates, trialkyl phosphates, dialkyl carbonates and/or formic acid orthoesters.

3. The process as claimed in claim 1, wherein the alkylating agent used is methyl chloride, methyl bromide and/or dimethyl sulfate.

4. The process as claimed in claim 1, wherein the base is selected from hydroxides, carbonates, bicarbonates, amides, alkoxides, and/or amine bases.

5. The process as claimed in claim 1, wherein the reaction in step a) is carried out in a two-phase system comprising aqueous alkali or alkaline-earth metal hydroxide or mixtures thereof and an organic solvent.

6. The process as claimed in claim 5, wherein the organic solvent used is selected from straight-chain or branched alkanes, alkyl-substituted aromatic solvents, water-immiscible or only partially water-miscible alcohols or ethers, alone or in combination with one another.

7. The process as claimed in claim 5, wherein the organic solvent employed is toluene, alone or in combination with alcohols.

8. The process as claimed in claim 1, wherein the reaction is carried out in the presence of a phase-transfer catalyst.

9. The process as claimed in claim 8, wherein the phase-transfer catalyst is a tetraalkylphosphonium halide, triphenylalkylphosphonium halide or tetraorganylammonium halide.

10. The process as claimed in claim 1, wherein the temperature during the reaction with the yellow phosphorus is from −20 to +80° C.

11. The process as claimed in claim 1, wherein the temperature during the reaction with the yellow phosphorus is from 0 to 30° C.

12. The process as claimed in claim 1, wherein the reaction is carried out under a pressure of from 0 to 10 bar.

13. The process as claimed in claim 1, wherein the principal constituents of the mixture from a) are esterified in step b) using a linear or branched alcohol of the general formula R—OH, where R is a linear or branched alkyl radical having 1 to 10 carbon atoms.

14. The process as claimed in claim 1, wherein the principal constituents of the mixture from a) are converted into a mixture of alkylphosphonous, phosphorous acids using a mineral acid, with the metal salt of the mineral acid simultaneously being precipitated, and the mixture of these acids subsequently being esterified.

15. The process as claimed in claim 1, wherein water formed during the esterification is removed by azeotropic distillation.

16. The process as claimed in claim 13, wherein the alcohol is n- or i-butanol, n-hexanol, ethylhexanol and/or amyl alcohol.

17. The process as claimed in claim 14, wherein the mineral acid is hydrochloric acid, sulfuric acid and/or phosphoric acid.

18. The process as claimed in claim 14, wherein the mineral acid is hydrochloric acid.

19. The process as claimed in claim 1, wherein phosphines which are formed in small amounts in step a) are removed by oxidation.

20. The process as claimed in claim 19, wherein hydrogen peroxide is used for the oxidation.

21. The process as claimed in claim 1, wherein the ester of the alkylphosphonous acid is removed by distillation in step c).

22. The process as claimed in claim 1, wherein the ester of the alkylphosphonous acid is n-butyl methylphosphonite, isobutyl methylphosphonite, n-hexyl methylphosphonite, 2-ethylhexyl methylphosphonite and/or amyl methylphosphonite.

23. The process as claimed in claim 1, wherein the free-radical initiator used in step d) is selected from azo compounds or peroxidic inorganic and/or peroxidic organic free-radical initiators.

24. The process as claimed in claim 23, wherein the azo compounds are cationic and/or non-cationic azo compounds.

25. The process as claimed in claim 24, wherein the cationic azo compounds are selected from 2,2'-azobis(2-amidinopropane) dihydrochloride or 2,2'-azobis(N,N'-dimethyleneisobutyramidine) dihydrochloride.

26. The process as claimed in claim 24, wherein the non-cationic azo compounds are selected from azobis(isobutyronitrile), 4,4'-azobis(4-cyanopentanoic acid) and/or 2,2'-azobis(2-methylbutyronitrile).

27. The process as claimed in claim 23, wherein the peroxidic inorganic free-radical initiators are selected from hydrogen peroxide, ammonium peroxodisulfate and/or potassium peroxodisulfate.

28. The process as claimed in claim 23, wherein the peroxidic organic free-radical initiators are selected from dibenzoyl peroxide, di-tert-butyl peroxide and/or peracetic acid.

29. The process as claimed in claim 1, wherein the free-radical initiators are metered in continuously during the reaction.

30. The process as claimed in claim 1, wherein the free-radical initiators are metered in continuously during the reaction as a solution in the olefin.

31. The process as claimed in claim 1, wherein the olefins used are linear or branched α-olefins.

32. The process as claimed in claim 1, wherein the olefins used have an internal double bond, cyclic or open-chain dienes and/or polyenes having 4 to 10 carbon atoms.

33. The process as claimed in claim 1, wherein the olefins used are ethylene, n- or i-propylene, n- or i-butene, n- or i-pentene, n- or i-hexene, n- or i-octene, 1-decene, 1,3-cyclooctadiene, 1,3 cyclopentadiene, dicyclopentadiene and/or 2,4,4-trimethylpentene isomer mixtures.

34. The process as claimed in claim 1, wherein the metals are Li, Na, K, Mg, Ca, Sr, Ba, Al, Ge, Sn, Sb, Bi, Zn, Ti, Zr, Mn, Fe and/or Ce.

35. The process as claimed in claim 1, wherein, in step e) the ester of the dialkylphosphinic acid is reacted directly with metal compounds to give the metal salt of the dialkylphosphinic acid.

36. The process as claimed in claim 1, wherein, in step e), the ester of the dialkylphosphinic acid is hydrolyzed to the dialkylphosphinic acid.

37. The process as claimed in claim 1, wherein, in step e), the ester of the dialkylphosphinic acid is hydrolyzed to the dialkylphosphinic acid and then converted to the metal salt of the dialkylphosphinic acid.

38. The process as claimed in claim 1, wherein, in step e), the ester of the dialkylphosphinic acid is hydrolyzed to the sodium salt of the dialkylphosphinic acid using sodium hydroxide solution.

39. The process as claimed in claim 1, wherein, in step e), the ester of the dialkylphosphinic acid is hydrolyzed to the sodium salt of the dialkylphosphinic acid with sodium hydroxide solution and then converted to the non-sodium metal salts of the dialkylphosphinic acid.

40. The process as claimed in claim 35, wherein the metal compounds are metal oxides, hydroxides, oxide hydroxides, sulfates, acetates, chlorides, nitrates and/or alkoxides.

41. The process as claimed in claim 35, wherein the metal compunds are aluminum hydroxide or aluminum sulfates.

* * * * *